(12) United States Patent
Liu et al.

(10) Patent No.: US 10,898,731 B2
(45) Date of Patent: *Jan. 26, 2021

(54) NEUTRON CAPTURE THERAPY SYSTEM

(71) Applicant: NEUBORON MEDTECH LTD., Jiangsu (CN)

(72) Inventors: Yuan-Hao Liu, Jiangsu (CN); Wei-Lin Chen, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 379 days.

This patent is subject to a terminal disclaimer.

(21) Appl. No.: 15/967,727

(22) Filed: May 1, 2018

(65) Prior Publication Data
US 2018/0243587 A1 Aug. 30, 2018

Related U.S. Application Data

(63) Continuation of application No. PCT/CN2016/102332, filed on Oct. 18, 2016.

(30) Foreign Application Priority Data

Nov. 12, 2015 (CN) .......................... 2015 1 0770609
Nov. 12, 2015 (CN) ...................... 2015 2 0901136 U (51) Int. Cl.
*A61N 5/10* (2006.01)
*G21K 5/04* (2006.01)

(52) U.S. Cl.
CPC ............ *A61N 5/1077* (2013.01); *A61N 5/10* (2013.01); *A61N 2005/109* (2013.01); *A61N 2005/1095* (2013.01)

(58) Field of Classification Search
CPC .. A61N 5/1081; A61N 5/10; A61N 2005/109; A61N 2005/1095; A61N 2005/1098; H05H 3/06; H05H 6/00
(Continued)

(56) References Cited

U.S. PATENT DOCUMENTS 9,889,320 B2 * 2/2018 Liu ...................... H05H 6/00
9,974,979 B2 * 5/2018 Liu ...................... A61N 5/1077
(Continued)

FOREIGN PATENT DOCUMENTS

CN  1569275 A  1/2005
CN  101521981 B  12/2011
(Continued)

OTHER PUBLICATIONS

International Search Report of PCT/CN2016/102332, dated Feb. 21, 2017.

*Primary Examiner* — Nicole M Ippolito
(74) *Attorney, Agent, or Firm* — Locke Lord LLP; Tim Tingkang Xia, Esq.

(57) ABSTRACT

The present disclosure provides a neutron capture therapy system including a beam shaping assembly. The beam shaping assembly includes a beam inlet; a neutron generator arranged into the beam shaping assembly, the neutron generator has nuclear reaction with an incident proton beam from the beam inlet to produce neutrons; a moderator adjacent to the neutron generator, the neutrons are moderated by the moderator to epithermal neutron energies; a reflector surrounding the neutron generator and the moderator, the reflector leads the deflected neutrons back to enhance epithermal neutron beam intensity; a beam outlet; and at least a movable member moving away from or close to the neutron generator, the movable member moves between a first position where the neutron generator is replaceable, and a second position where the neutron generator is irreplaceable. The neutron capture therapy system has a simple structure, and the neutron generator is easy to be replaced.

20 Claims, 5 Drawing Sheets

(58) Field of Classification Search
USPC .......................................... 250/492.1, 492.3
See application file for complete search history.

(56) References Cited

U.S. PATENT DOCUMENTS

| | | | | |
|---|---|---|---|---|
| 10,124,192 B2* | 11/2018 | Liu | ........................ | H05H 6/00 |
| 10,328,286 B2* | 6/2019 | Liu | .................... | A61N 5/1042 |
| 10,434,333 B2* | 10/2019 | Liu | ........................ | A61N 5/10 |
| 10,610,704 B2* | 4/2020 | Liu | ........................ | G21G 4/02 |
| 10,617,893 B2* | 4/2020 | Liu | .................... | C04B 35/645 |
| 10,639,499 B2* | 5/2020 | Liu | ...................... | G21K 1/067 |
| 2018/0193673 A1* | 7/2018 | Liu | ........................ | H05H 6/00 |

FOREIGN PATENT DOCUMENTS

| | | |
|---|---|---|
| CN | 103052425 A | 4/2013 |
| CN | 205235192 U | 5/2016 |
| JP | 2007240330 A | 9/2007 |
| JP | 2008022920 A | 2/2008 |
| JP | 2009204428 A | 9/2009 |

\* cited by examiner

NEUTRON CAPTURE THERAPY SYSTEM

RELATED APPLICATION INFORMATION

This application is a continuation of International Application No. PCT/CN2016/102332, filed on Oct. 18, 2016, which claims priority to Chinese Patent Application No. 201510770609.1, filed on Nov. 12, 2015; Chinese Patent Application No. 201520901136.X, filed on Nov. 12, 2015, the disclosures of which are hereby incorporated by reference.

FIELD OF THE DISCLOSURE

The present disclosure relates generally to a neutron capture therapy system, and, more particularly, to a neutron capture therapy system with a replaceable neutron generator.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radio resistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

According to accelerator-based boron neutron capture therapy, a neutron generator which is used for performing nuclear reaction with proton beams to generate neutron beams, and the neutron generator needs to withstand radiation and radio activation of acceleration protons and is thus damaged to a certain extent. Since the neutron generator has a quite important influence on the quality of the generated neutron beams, the neutron generator must be replaced periodically so as to reduce the influence of the neutron generator on the quality of the neutron beams.

However, a moderator for the accelerator-based boron neutron capture therapy in the prior art is most cylindrical, the neutron generator is generally arranged in the moderator with a certain depth. When being damaged and needing to be replaced, the neutron generator can be detached only after a large number of steps have been taken, so that the neutron generator cannot be replaced easily.

The statements in this section merely provide background information related to the present disclosure and may not constitute prior art.

SUMMARY

In order to replace the neutron generator easily, an aspect of the present disclosure provides a beam shaping assembly for neutron capture therapy includes: a beam inlet; a neutron generator arranged in the beam shaping assembly, the neutron generator has nuclear reaction with an incident proton beam from the beam inlet to produce neutrons; a moderator adjoining to the neutron generator, the neutrons are moderated by the moderator to epithermal neutron energies; a reflector surrounding the neutron generator and the moderator, the reflector leads the deflected neutrons back to enhance the epithermal neutron beam intensity; a beam outlet; and at least a movable member moving away from or close to the neutron generator, wherein the movable member moves between a first position where the neutron generator is replaceable and a second position where the neutron generator is irreplaceable.

Implementations of this aspect may include one or more of the following features.

The movable member is part of the reflector or a combination of part of the reflector and part of the moderator.

The reflector defines a first linear height, the movable member defines a second linear height, the neutron generator defines a third linear height, and the second linear height is smaller than or equal to the first linear height and is greater than the third linear height.

The movable member defines a symmetry plane, the movable member is symmetrical with respect to the symmetry plane, and the symmetry plane passes through an axis of the neutron generator.

More particularly, the reflector includes a first connecting part which includes a first connecting surface and a first junction surface; the movable member includes a second connecting part which includes a second connecting surface and a second junction surface; the first connecting surface connects with the second connecting surface and is overlapped with the second connecting surface, the first junction surface connects with the second junction surface and is overlapped with the second junction surface, and the second junction surface is overlapped with the plane where the axis of the neutron generator is in.

More particularly, when the second liner height is smaller than the first linear height and greater than the third height, the first connecting surface and the first junction surface are overlapped, the second connecting surface and the second junction surface are overlapped; when the second linear height is equal to the first linear height, the first connecting surface and the first junction surface are connected but are located in different planes, the second connecting surface and the second junction surface are connected but are located in different planes, the first connecting surface connects with the second connecting surface and is overlapped with the second connecting surface, and the first junction surface connects with the second junction surface and is overlapped with the second junction surface.

Further, the neutron capture therapy system further includes a driving assembly; the driving assembly includes at least a gate to support the movable member, and a guide rail for allowing the gate to move away from or close to the neutron generator; when the gate moves away from the beam shaping assembly, the movable member moves to the first position; and when the gate moves close to the beam shaping assembly, the movable member moves to the second position.

More particularly, the guide rail is arranged outside the beam shaping assembly, the gate moves away from or close to the beam shaping assembly along the guide rail.

Further, the guide rail is arranged outside the beam shaping body, the driving assembly further includes supporting a frame, one end of the supporting frame is used for supporting the gate, the other end of the supporting frame moves in the guide rail, and the gate moves away from or close to the beam shaping assembly as the supporting frame moves along the guide rail.

More particularly, when the second linear height is smaller than the first linear height and is greater than the third linear height, a guide rail is arranged in the reflector, and the movable member is arranged in the beam shaping assembly and moves away from or close to the neutron generator through the guide rail.

In another aspect of the present disclosure, a beam shaping assembly for neutron capture therapy is provided for replacing the neutron generator easily. The beam shaping assembly includes a beam inlet; a neutron generator arranged in the beam shaping assembly, wherein the neutron generator has nuclear reaction with an incident proton beam from the beam inlet to produce neutrons; a moderator adjoining to the neutron generator, wherein the neutrons are moderated by the moderator to epithermal neutron energies; a reflector surrounding the moderator, wherein the reflector leads the deflected neutrons back to enhance the epithermal neutron beam intensity; a beam outlet; and at least a movable member moving away from or close to the neutron generator, wherein the movable member moves between a first position where the neutron generator is replaceable and a second position where the neutron generator is irreplaceable, and wherein the movable member defines a curved surface, when the moveable member moves away from the beam shaping assembly, a notch is shaped on the beam shaping assembly where the neutron generator is replaced; and when the moveable member moves close to the beam shaping assembly, the curved surface surrounds at least half of the neutron generator.

Further, the movable member is a part of the reflector or a combination of part of the reflector and part of the moderator.

More particularly, the reflector defines a first linear height, the movable member defines a second linear height, the neutron generator defines a third linear height, and the second linear height is smaller than or equal to the first linear height and is greater than the third linear height.

Further, the movable member defines a symmetry plane, the movable member is symmetrical with respect to the symmetry plane; the symmetry plane passes through an axis of the neutron generator.

More particularly, the neutron capture therapy system further includes a driving assembly; the driving assembly includes at least a gate for supporting the movable member, and a guide rail for allowing the gate to move away from or close to the neutron generator; the guide rail is arranged outside the beam shaping assembly, and the gate moves away from or close to the beam shaping assembly through the guide rail, the movable member moves away from or close to the neutron generator along the guide rail.

More particularly, the driving assembly further includes a supporting frame, one end of the supporting frame supports the gate, the other end of the supporting frame moves in the guide rail, and the gate moves away from or close to the beam shaping assembly as the supporting frame moves along the guide rail.

More particularly, when the second linear height is smaller than the first linear height and is greater than the third linear height, a guide rail is arranged in the reflector, and the movable member is arranged in the beam shaping assembly and moves away from or close to the neutron generator through the guide rail.

In yet another aspect of the present disclosure, a beam shaping assembly for neutron capture therapy is provided for replacing the neutron generator. The beam shaping assembly for neutron capture therapy includes a beam inlet; a neutron generator arranged in the beam shaping assembly, wherein the neutron generator has nuclear reaction with an incident proton beam from the beam inlet to produce neutrons; a moderator adjoining to the neutron generator, wherein the neutrons are moderated by the moderator to epithermal neutron energies; a reflector surrounding the moderator, wherein the reflector leads the deflected neutrons back to enhance epithermal neutron beam intensity, and the reflector further defines a first connecting surface and a first junction surfaces connects to the first connecting surface; a beam outlet; and at least a movable member moving away from or close to the neutron generator, wherein the movable member moves between a first position where the neutron generator is replaceable and a second position where the neutron generator is irreplaceable, and wherein the movable member defines a second connecting surface and a second junction surface connected with the second connecting surface, the second connecting surface is overlapped with the first connecting surface, the second junction surface is overlapped with the first junction surface, when the moveable member moves away from the neutron generator, the first connecting surface is separated from the second connecting surface, the first junction surface is separated from the second junction surface, and the neutron generator is replaceable.

Further, the first connecting surface is inclined to the first junction surface, the second connecting surface is inclined to the second junction surface.

More particularly, the second junction surface includes a recess, the first junction surface includes a protrusion for engaging to the recess in a form-fitting manner.

Further areas of applicability will become apparent from the description provided herein. It should be understood that the description and specific examples are intended for purposes of illustration only and are not intended to limit the scope of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, and high temperature resistance etc. But in reality, no nuclear reactions may satisfy all requests, the neutron generator is certainly damaged after being subjected to the impact and radiation of the accelerated protons, and further, the neutron generator has a quite important influence on the quality of neutron beams, so replacing the neutron generator periodically or according to the damaged condition of the neutron generator is quite necessary. A neutron capture therapy system with a replaceable neutron generator is described as below.

Figure 1:
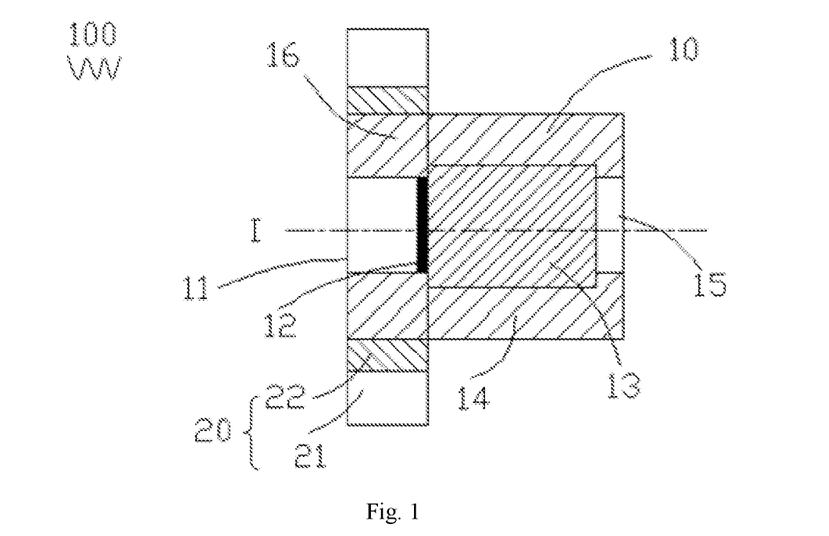
FIG. 1 is a schematic view of a neutron capture therapy system.

FIG. 1 is a schematic view of the neutron capture therapy system 100 according to the present disclosure. The neutron capture therapy system 100 includes a beam shaping assembly 10 and a driving assembly 20.

The beam shaping assembly 10 includes a beam inlet 11, a neutron generator 12, a moderator 13 adjacent to the neutron generator 12, a reflector 14 surrounding the neutron generator 12 and the moderator 13, and a beam outlet 15. The proton beams enter into the beam inlet 11 and have nuclear reaction with the neutron generator 12 to generate neutrons, the moderator 13 moderates the neutrons generated by the neutron generator 12, and the reflector 14 leads deflected neutrons back to the moderator 13 so as to improve the intensity of epithermal neutron beams.

The reflector 14 includes at least one movable member 16 capable of moving away from or close to the neutron generator 12. The movable member 16 moves between a first position L1 and a second position L2 (refer to FIG. 2a and FIG. 2b). When the movable member 16 is located in the first position L1, the neutron generator 12 is replaceable; and when the movable member 16 is located in the second position L2, the neutron generator 12 is irreplaceable. Specifically, when the movable member 16 moves away from the neutron generator 12 to the first position L1, the neutron generator 12 is exposed out of the beam shaping assembly 10, and the neutron generator 12 can be taken out to be replaced; and after a new neutron generator 12 is mounted in the beam shaping assembly 10, the movable member 16 moves close to the neutron generator 12 and located at the second position L2 (the movable member surrounds the neutron generator 12, so that the neutron generator 12 is irreplaceable), and then both the movable member 16 and the reflector 14 lead the deflected neutrons back to the moderator in the subsequent neutron capture therapy process.

The movable member 16 may be a part of the reflector or a combination of part of the reflector and part of the moderator. When the movable member 16 is a part of the reflector, the neutron generator 12 is arranged in front of the moderator 13 and is surrounded by the reflector 14, the moderator 13 is adjacent to the rear portion of the neutron generator 12, at this moment, only part of the reflector needs to be arranged as a movable structure (named the movable member), and the neutron generator is replaced after the movable member moves away from the neutron generator. When the movable member 16 is a combination of a part of the reflector and a part of the moderator, the neutron generator 12 is embedded into the moderator 13 and is surrounded by the moderator 13, and at this moment, in order to replace the neutron generator 12, part of the reflector and part of the moderator surrounding neutron generator 12 need to be arranged as movable structure (named the movable member), and the neutron generator 12 is replaceable.

Figure 3A:
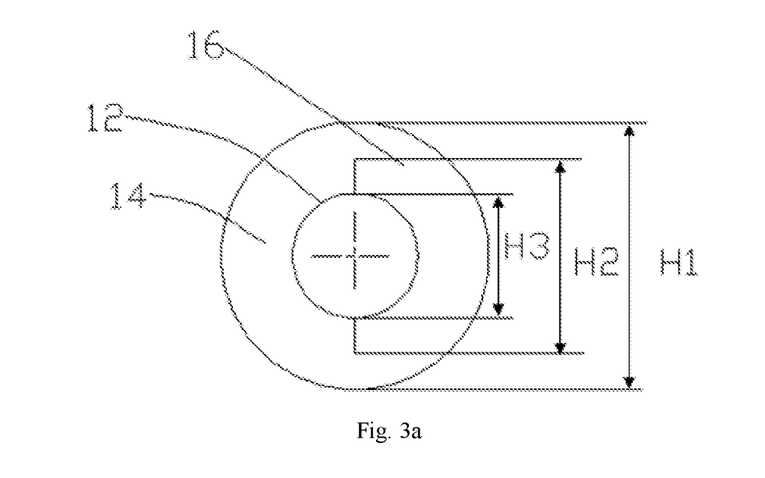
FIG. 3a is a schematic view of a movable member located in a second position, wherein the second junction surface of the movable member is connected with the first junction surface of a reflector and overlaps with one of the planes where the axis of a neutron generator is located.
Figure 3B:
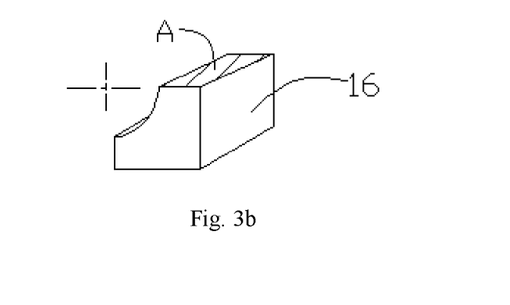
FIG. 3b is a section view of movable member along a symmetry plane A according to the present disclosure.

Referring to FIG. 3a and FIG. 3b, for the convenience of the replacement of the neutron generator 12, preferably, the movable member 16 is a symmetrical member. The symmetrical member is provided with a symmetry plane A, the symmetrical member is symmetric with respect to the symmetry plane A, and the symmetry plane A passes through an axis I of the neutron generator 12. The reflector 14 defines a first linear height H1, the movable member 16 defines a second linear height H2, the neutron generator 12 defines a third linear height H3, and the second linear height H2 is smaller than or equal to the first linear height H1 and is greater than the third linear height H3.

Figure 4A:
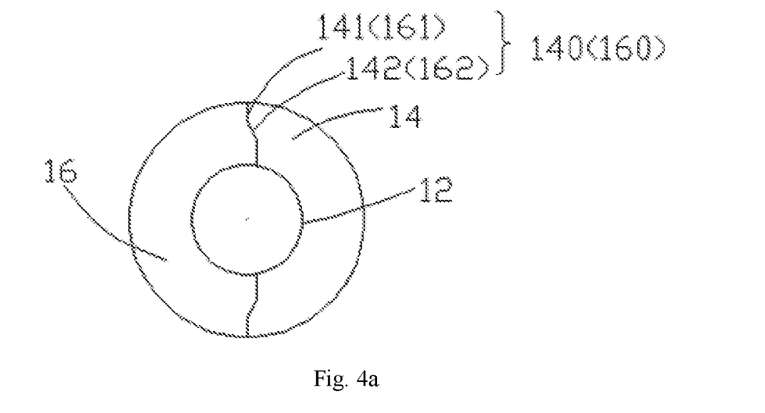
FIG. 4a is a schematic view of a movable member located in a second position, wherein the first connecting surface is inclined to the first junction surface.
Figure 4B:
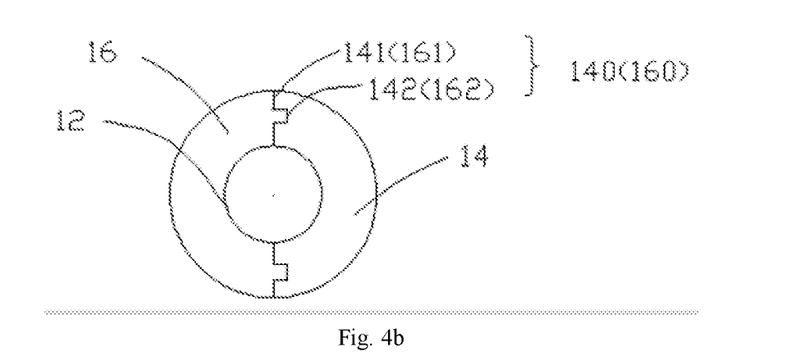
FIG. 4b a schematic view of a movable member located in a second position, wherein a recess of the movable member and a protrusion of the reflector are engaged in a form-fitting manner.

Referring to FIG. 4a and FIG. 4b, the reflector 14 is further provided with a first connecting part 140, and the movable member 16 is provided with a second connecting part 160. The first connecting part 140 is provided with a first connecting surface 141 and a first junction surface 142 connected to the first connecting surface 141, and the second connecting part 160 is provided with a second connecting surface 161 and second junction surface 162 connected with the second connecting surface 161.

When the second linear height H2 is smaller than the first linear height H1 and is greater than the third linear height H3, the first connecting surface 141 and the first junction surface 142 are overlapped, the second connecting surface 161 and the second junction surface 162 are overlapped, the second junction surface 162 is connected with the first junction surface 142 and are overlapped with an optional plane where the axis of the neutron generator 12 is located (please refer to FIG. 3a). In this example, the movable member 16 is a part of the reflector 14. In this situation, when the movable member 16 moves away from the neutron generator 12 to the first position L1, a notch is formed in the reflector 14 by the movable member 16, and the neutron generator 12 is exposed out of the notch, and the neutron generator 12 is replaced at the notch; and when the movable member 16 moves close to the neutron generator 12 to the second position L2, the movable member 16 surrounds the neutron generator 12, and the movable member 16 and the reflector 14 lead the deflected neutrons back to the moderator in the subsequent neutron capture therapy process.

When the second linear height H2 of the movable member 16 is equal to the first linear height H1 of the reflector 14, the movable member 16 is half of the reflector 14 surrounding the neutron generator 12. To reduce particles or radiation leaked at the connecting positions of the movable member 16 and the reflector 14 in the subsequent neutron capture therapy process, preferably, the first connecting surface 141 and the first junction surface 142 of the reflector 14 are located in different planes, the second connecting surface 161 and the second junction surface 162 of the movable member 16 is located in different planes, the first connecting surface 141 and the second connecting surface 161 are engaged, and the first junction surface 142 and the second junction surface 162 are engaged. The first connecting part 140 and the second connecting part 160 are specifically arranged as below (please refer to FIG. 4a): the second connecting surface 161 is inclined to the second junction surface 162; the first junction surface 142 is inclined to the first connecting surface 141. When the movable member 16 surrounds the neutron generator 12, the second junction surface 162 and the first junction surface 142 are engaged, and the second connecting surface 161 and the first connecting surface 141 are engaged. The first connecting part 140 and the second connecting part 160 are also be arranged as below (please refer to FIG. 4b): the second junction surface 162 includes a recess concavely formed in the second connecting surface 161, and the first junction surface 142 includes a protrusion protruding out of the first connecting surface 141, and when the movable member 16 surrounds the neutron generator 12, the recess and the protrusion are engaged in a form-fitting manner.

The structure of the driving assembly 20 is described in detail as below. In addition, since the structure of the movable member 16 is already described above in detail, the description is not repeated hereinafter. During actual application, the structure of the movable member 16 as described above can be combined with the driving assembly 20 described below. Though an embodiment described below is illustrated based on the reflector provided with the two movable members, one movable member can also be used if the one movable member 16 can realize the replacement of the neutron generator 12.

Figure 2A:
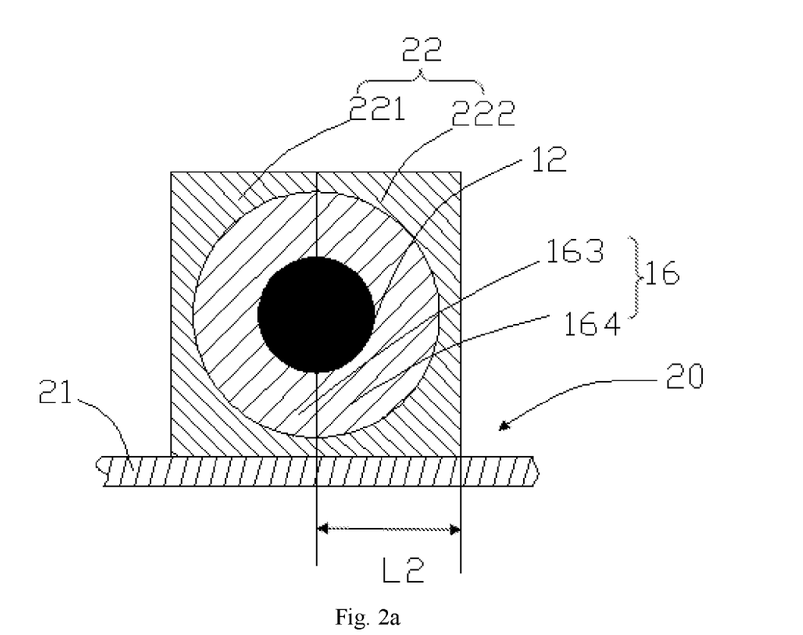
FIG. 2a is a schematic view of a movable member located in a second position, wherein the movable member is irreplaceable.
Figure 2B:
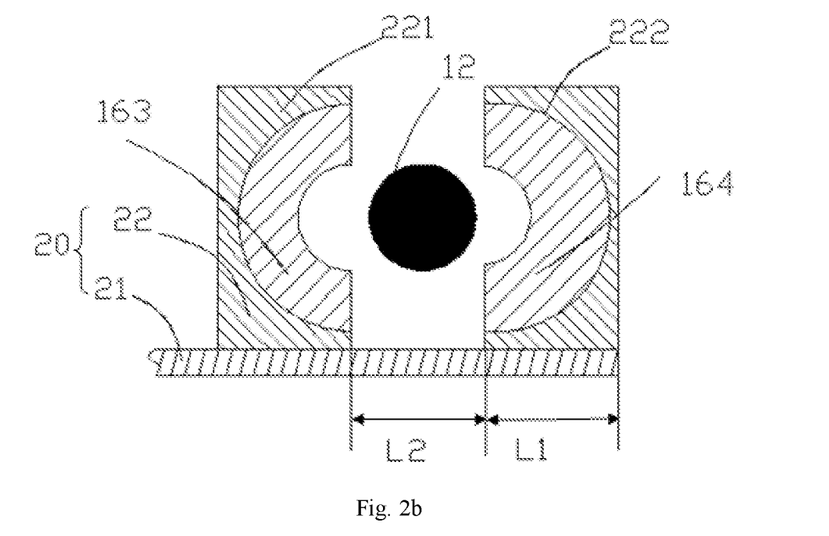
FIG. 2b is a schematic view of a movable member located in a first position, wherein the movable member is replaceable.

A first embodiment of the present disclosure is also shown in FIG. 2a and FIG. 2b, and is described based on the reflector 14 provided with the two movable members 16 (namely a first movable member 163 and a second movable member 164) located on the two sides of the neutron generator 12 and mutually connected. The driving assembly 20 includes a guide rail 21 arranged outside the beam shaping assembly 10 and gates 22 used for supporting the movable members 16, and the gates 22 move in the guide rail 21 to drive the movable members 16 to move away from or close to the neutron generator 12. The movable members 16 include the first movable member 163 and the second movable member 164, the gates 22 include a first gate 221 and a second gate 222 which can move along the guide rail 21, the first gate 221 supports the first movable member 163, and the second gate 222 supports the second movable member 164. The first gate 221 and the second gate 222 move in the guide rail 21 to drive the first movable member 163 and the second movable member 164 to move away from or close to the neutron generator 12 correspondingly. When both the first gate 221 and the second gate 222 move away from the beam shaping assembly 10 to the first positions L1, the first movable member 163 and the second movable member 164 also move away from the neutron generator 12, and the neutron generator 12 is exposed out of the beam shaping assembly 10 and can be replaced; and when both the first gate 221 and the second gate 222 move close to the neutron generator 12 to the second positions L2, the first movable member 163 and the second movable member 164 also move close to the neutron generator 12 until the first movable member 163 and the second movable member 164 surround the neutron generator 12, and the first movable member 163 and the second movable member 164 are used for leading the deflected neutrons back in the subsequent neutron capture therapy process.

To simplify the structural design, preferably, the first movable member 163 and the second movable member 164 are the same in structure, and the first gate 221 and the second gate 222 are also the same in structure. To simplify the introduction hereinafter, both the first movable member 163 and the second movable member 164 are called the movable member 16, and both the first gate 221 and the second gate 222 are called the gate 22.

Figure 5A:
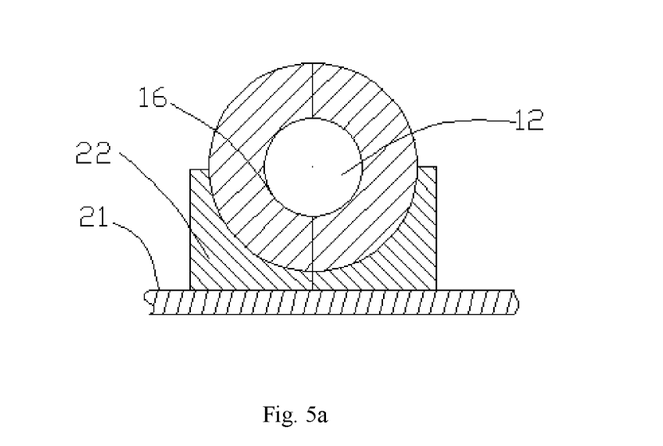
FIG. 5a is a schematic view of another embodiment of the movable member, wherein the movable member is partially embedded into a gate.
Figure 5B:
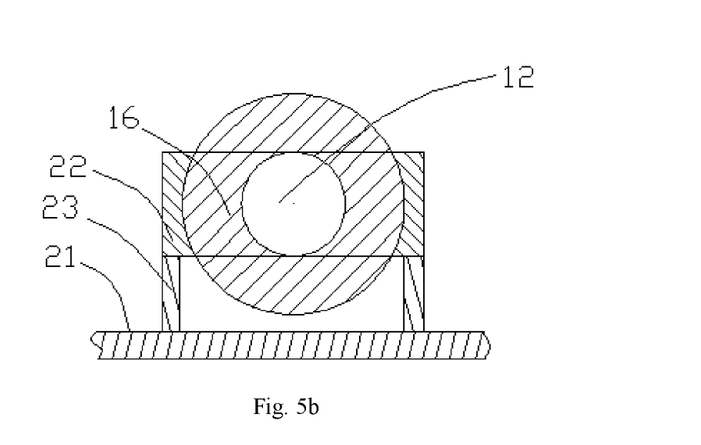
FIG. 5b is a schematic view of another embodiment of the movable member, wherein a driving assembly includes a supporting frame.

The gates 22 can be of various structures. In the present embodiment, when the second linear height H2 of the movable member 16 is equal to the first linear height H1 of the reflector 14, the gates 22 surround the movable members 16, the movable members 16 can be considered to be embedded into the gates 22, motion of the gates 22 in the guide rail 21 is equivalent to opening-closing motion of the gates 22, and the movable members 16 get away from or close to the neutron generator 12 as the gates 22 are opened and closed. Preferably, the gates 22 are made of concrete. For sure, in order to save space or cost, half or even a smaller part of the movable members 16 can be embedded into the gates 22 (please refer to FIG. 5a) as long as the gates 22 of this design can support the movable members 16 and can drive the movable members 16 to move away from or close to the neutron generator 12. When the second linear height H2 of the movable members 16 is smaller than the first linear height H1 of the reflector 14, supporting frames 23 can further be arranged between the gates 22 and the guide rail 21 (please refer to FIG. 5b). One ends of the supporting frames 23 are fixed to the gates 22, and the other ends of the supporting frames 23 move in the guide rail 21 to get away from or close to the beam shaping assembly 10. The movable members 16 move away from or close to the neutron generator 12 as the gates 22 move along the guide rail 21. That is, the gates 22 are driven to move by means of movement of the supporting frames 23 in the guide rail 21, so that the gates 22 need to be designed into a sufficiently large size to move directly in the guide rail 21 is avoided, and accordingly the size of the gates 22 is reduced.

Figure 6:
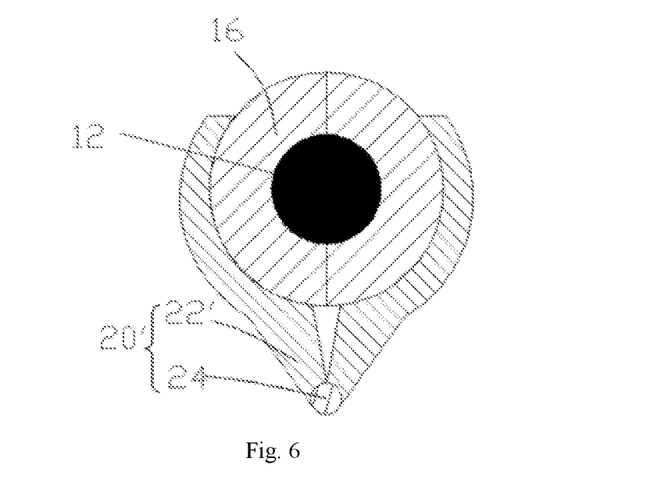
FIG. 6 is a schematic view of a second embodiment of the present disclosure.

FIG. 6 is a schematic view of a second embodiment of the present disclosure. A driving assembly 20 includes a rotating member 24 (such as a shaft) and gates 22' fixedly held to the rotating member 24. The rotating member 24 is located under a beam shaping assembly 10, and an axis of the rotating member 24 is parallel to that of a neutron generator 12. The gates 22' rotate up and down around the rotating member 24. When the gates 22' move downwards, the gates 22' drive movable members 16 to move away from the neutron generator 12, the neutron generator 12 is exposed out, and the neutron generator 12 can be replaced; and when the gates 22' rotate upwards, the gates 22' drive the movable members 16 to move close to the neutron generator 12, and the movable members 16 surround the neutron generator 12, and is used for leading the deflected neutrons back in the subsequent neutron capture therapy process.

Figure 7:
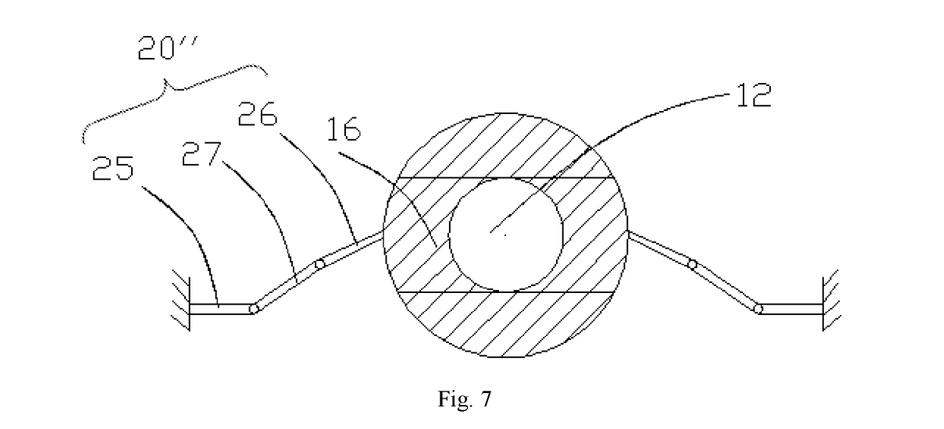
FIG. 7 is a schematic view of a third embodiment of the present disclosure.

FIG. 7 is a schematic view of a third embodiment of the present disclosure. A driving assembly 20 in the present embodiment includes first connecting rods 25 fixed to the outside of the beam shaping assembly 10, second connecting rods 26 connected to movable members 16, and third connecting rods 27 enable the first connecting rods 25 and the second connecting rods 26 to be connected, the third connecting rods 27 move to drive the second connecting rods 26 to move, and the movable members 16 move away from or close to the neutron generator 12 as the second connecting rods 26 move.

Figure 8:
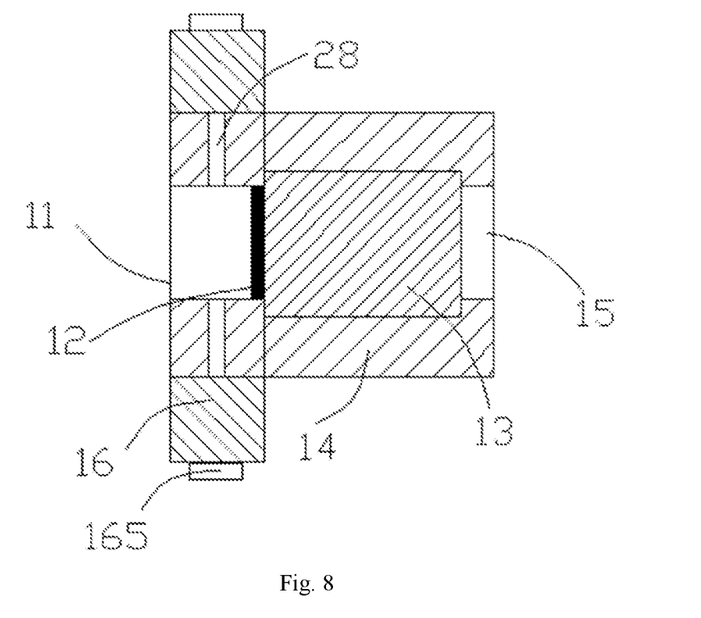
FIG. 8 is a schematic view of a fourth embodiment of the present disclosure.

FIG. 8 is a schematic view of a fourth embodiment of the present disclosure. When the second linear height H2 of movable members 16 is smaller than a first linear height H1 of the reflector 14 (particularly when the second linear height H2 of the movable members 16 is smaller than a third linear height H3 of a neutron generator 12), the guide rail 28 can be arranged in the reflector 14, and handles 165 can be arranged on the outer surfaces of the movable members 16, so that the movable members 16 are driven to move along the guide rail 28 to get away from or close to the neutron generator 12 by pulling and pushing the handles 165. Certainly, the driving assemblies in the first embodiment to the third embodiment can also be applied to the fourth embodiment for replacing the handles, which is not described in detail here.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A neutron capture therapy system, comprising a beam shaping assembly, wherein the beam shaping assembly comprises,
   a beam inlet;
   a neutron generator arranged in the beam shaping assembly, wherein the neutron generator has nuclear reaction with an incident proton beam from the beam inlet to produce neutrons;
   a moderator adjoining to the neutron generator, wherein the neutrons are moderated by the moderator to epithermal neutron energies;
   a reflector surrounding the neutron generator and the moderator, wherein the reflector leads the deflected neutrons back to enhance the epithermal neutron beam intensity;
   a beam outlet; and
   at least a movable member moving away from or close to the neutron generator, wherein the movable member moves between a first position where the neutron generator is replaceable and a second position where the neutron generator is irreplaceable.

2. The neutron capture therapy system according to claim 1, wherein the movable member is part of the reflector or a combination of part of the reflector and part of the moderator.

3. The neutron capture therapy system according to claim 1, wherein the reflector defines a first linear height, the movable member defines a second linear height, the neutron generator defines a third linear height, and the second linear height is smaller than or equal to the first linear height and is greater than the third linear height.

4. The neutron capture therapy system according to claim 3, wherein the movable member defines a symmetry plane, the movable member is symmetrical with respect to the symmetry plane, and the symmetry plane passes through an axis of the neutron generator.

5. The neutron capture therapy system according to claim 2, wherein the reflector includes a first connecting part which comprises a first connecting surface and a first junction surface; the movable member includes a second connecting part which comprises a second connecting surface and a second junction surface; the first connecting surface connects with the second connecting surface and is overlapped with the second connecting surface, the first junction surface connects with the second junction surface and is overlapped with the second junction surface, and the second junction surface is overlapped with the plane where the axis of the neutron generator is in.

6. The neutron capture therapy system according to claim 3, wherein when the second liner height is smaller than the first linear height and greater than the third height, the first connecting surface and the first junction surface are overlapped, the second connecting surface and the second junction surface are overlapped; when the second linear height is equal to the first linear height, the first connecting surface and the first junction surface are connected but are located in different planes, the second connecting surface and the second junction surface are connected but are located in different planes, the first connecting surface connects with the second connecting surface and is overlapped with the second connecting surface, and the first junction surface connects with the second junction surface and is overlapped with the second junction surface.

7. The neutron capture therapy system according to claim 1, wherein the neutron capture therapy system further comprises a driving assembly; the driving assembly comprises at least a gate to support the movable member, and a guide rail for allowing the gate to move away from or close to the neutron generator; when the gate moves away from the beam shaping assembly, the movable member moves to the first position; and when the gate moves close to the beam shaping assembly, the movable member moves to the second position.

8. The neutron capture therapy system according to claim 7, wherein the guide rail is arranged outside the beam shaping assembly, the gate moves away from or close to the beam shaping assembly along the guide rail.

9. The neutron capture therapy system according to claim 6, wherein the guide rail is arranged outside the beam shaping body, the driving assembly further comprises supporting a frame, one end of the supporting frame is used for supporting the gate, the other end of the supporting frame moves in the guide rail, and the gate moves away from or close to the beam shaping assembly as the supporting frame moves along the guide rail.

10. The neutron capture therapy system according to claim 2, wherein when the second linear height is smaller than the first linear height and is greater than the third linear height, a guide rail is arranged in the reflector, and the movable member is arranged in the beam shaping assembly and moves away from or close to the neutron generator through the guide rail.

11. A neutron capture therapy system, comprising a beam shaping assembly, wherein the beam shaping assembly comprises,
a beam inlet,
a neutron generator arranged in the beam shaping assembly, wherein the neutron generator has nuclear reaction with an incident proton beam from the beam inlet to produce neutrons;
a moderator adjoining to the neutron generator, wherein the neutrons are moderated by the moderator to epithermal neutron energies;
a reflector surrounding the moderator, wherein the reflector leads the deflected neutrons back to enhance the epithermal neutron beam intensity;
a beam outlet; and
at least a movable member moving away from or close to the neutron generator, wherein the movable member moves between a first position where the neutron generator is replaceable and a second position where the neutron generator is irreplaceable, and wherein the movable member defines a curved surface, when the moveable member moves away from the beam shaping assembly, a notch is shaped on the beam shaping assembly where the neutron generator is replaced; and when the moveable member moves close to the beam shaping assembly, the curved surface surrounds at least half of the neutron generator.

12. The neutron capture therapy system according to claim 11, wherein the movable member is a part of the reflector or a combination of part of the reflector and part of the moderator.

13. The neutron capture therapy system according to claim 11, wherein the reflector defines a first linear height, the movable member defines a second linear height, the neutron generator defines a third linear height, and the second linear height is smaller than or equal to the first linear height and is greater than the third linear height.

14. The neutron capture therapy system according to claim 11, wherein the movable member defines a symmetry plane, the movable member is symmetrical with respect to the symmetry plane; the symmetry plane passes through an axis of the neutron generator.

15. The neutron capture therapy system according to claim 11, wherein the neutron capture therapy system further comprises a driving assembly; the driving assembly comprises at least a gate for supporting the movable member, and a guide rail for allowing the gate to move away from or close to the neutron generator; the guide rail is arranged outside the beam shaping assembly, and the gate moves away from or close to the beam shaping assembly through the guide rail, the movable member moves away from or close to the neutron generator along the guide rail.

16. The neutron capture therapy system according to claim 15, wherein the driving assembly further comprises a supporting frame, one end of the supporting frame supports the gate, the other end of the supporting frame moves in the guide rail, and the gate moves away from or close to the beam shaping assembly as the supporting frame moves along the guide rail.

17. The neutron capture therapy system according to claim 11, wherein when the second linear height is smaller than the first linear height and is greater than the third linear height, a guide rail is arranged in the reflector, and the movable member is arranged in the beam shaping assembly and moves away from or close to the neutron generator through the guide rail.

18. A neutron capture therapy system, comprising a beam shaping assembly, wherein the beam shaping assembly comprises,
a beam inlet;
a neutron generator arranged in the beam shaping assembly, wherein the neutron generator has nuclear reaction with an incident proton beam from the beam inlet to produce neutrons;
a moderator adjoining to the neutron generator, wherein the neutrons are moderated by the moderator to epithermal neutron energies;
a reflector surrounding the moderator, wherein the reflector leads the deflected neutrons back to enhance the epithermal neutron beam intensity, and wherein the reflector includes a first connecting surface and a first junction surfaces connects to the first connecting surface;
a beam outlet; and
at least a movable member moving away from or close to the neutron generator, wherein the movable member moves between a first position where the neutron generator is replaceable and a second position where the neutron generator is irreplaceable, and wherein the movable member defines a second connecting surface and a second junction surface connected with the second connecting surface, the second connecting surface is overlapped with the first connecting surface, the second junction surface is overlapped with the first junction surface, when the moveable member moves away from the neutron generator, the first connecting surface is separated from the second connecting surface, the first junction surface is separated from the second junction surface, and the neutron generator is replaceable.

19. The neutron capture therapy system according to claim 18, wherein the first connecting surface is inclined to the first junction surface, the second connecting surface is inclined to the second junction surface.

20. The neutron capture therapy system according to claim 18, wherein the second junction surface includes a recess, the first junction surface includes a protrusion for engaging to the recess in a form-fitting manner.

* * * * *